United States Patent
Van-Dinh et al.

(10) Patent No.: US 11,090,365 B2
(45) Date of Patent: Aug. 17, 2021

(54) COMPOSITION AND METHODS FOR TREATING BONE AND JOINT DISEASE INCLUDING EXTRACT FROM CROCODILOS REPTILIA AND HERBS

(71) Applicant: SVK Herbal Corporation, Ho Chi Minh (VN)

(72) Inventors: Cuong Van-Dinh, San Jose, CA (US); Nam Van Tran, Ho Chi Minh (VN); Phuong Chien Le, Ho Chi Minh (VN); Hai Hoang Nguyen, Ho Chi Minh (VN)

(73) Assignee: SVK Herbal Corporation, Ho Chi Minh (VN)

( * ) Notice: Subject to any disclaimer, the term of this patent is extended or adjusted under 35 U.S.C. 154(b) by 0 days.

(21) Appl. No.: 16/535,873

(22) Filed: Aug. 8, 2019

(65) Prior Publication Data

US 2021/0038699 A1 Feb. 11, 2021

(51) Int. Cl.

| | |
|---|---|
| *A61K 38/39* | (2006.01) |
| *A61K 36/19* | (2006.01) |
| *A61K 36/28* | (2006.01) |
| *A61K 36/126* | (2006.01) |
| *A61K 36/07* | (2006.01) |
| *A61P 19/10* | (2006.01) |
| *A61L 33/06* | (2006.01) |
| *A61K 33/42* | (2006.01) |
| *A61P 19/08* | (2006.01) |
| *A61P 19/02* | (2006.01) |
| *A61K 9/00* | (2006.01) |
| *A61K 33/06* | (2006.01) |

(52) U.S. Cl.
CPC ............ *A61K 38/39* (2013.01); *A61K 9/0053* (2013.01); *A61K 33/06* (2013.01); *A61K 33/42* (2013.01); *A61K 36/07* (2013.01); *A61K 36/126* (2013.01); *A61K 36/19* (2013.01); *A61K 36/28* (2013.01); *A61P 19/02* (2018.01); *A61P 19/08* (2018.01); *A61P 19/10* (2018.01)

(58) Field of Classification Search
CPC . A61K 36/00; A61K 8/36; A61K 8/65; A61K 36/126; A61K 38/39; A61P 19/08; A61P 19/02

See application file for complete search history.

(56) References Cited

U.S. PATENT DOCUMENTS

| | | |
|---|---|---|
| 6,350,476 B1 | 2/2002 | Hou |
| 2008/0069862 A1 | 3/2008 | Hurwitz |

FOREIGN PATENT DOCUMENTS

| | | | |
|---|---|---|---|
| CN | 101022823 | | 8/2007 |
| CN | 101248882 A | * | 8/2008 |
| CN | 102108098 A | * | 6/2011 |
| CN | 103099842 A | * | 5/2013 |
| CN | 103445140 A | * | 12/2013 |
| CN | 104840599 A | * | 8/2015 |
| CN | 105452269 A | | 3/2016 |
| CN | 103099842 A | | 1/2017 |
| CN | 106344834 A | * | 1/2017 |
| CN | 106794196 A | | 5/2017 |
| CN | 107929557 A | | 4/2018 |
| EP | 1416966 B1 | | 9/2009 |
| WO | 2007/139887 | | 12/2007 |

OTHER PUBLICATIONS

Zhang et al (Bone Research, 2016, vol. 4, pp. 1-14) (Year: 2016).*
CN-101248882-A (Espacenet English translation, downloaded Jul. 2020) (Year: 2020).*
CN-103099842-A (Espacenet English translation, downloaded Jul. 2020) (Year: 2020).*
CN-106344834-A (Espacenet English translation, downloaded Jul. 2020) (Year: 2020).*
CN-104840599-A (Espacenet English translation, downloaded Jul. 2020) (Year: 2020).*
CN-103445140-A (Espacenet English translation, downloaded Jul. 2020) (Year: 2020).*
CN-102108098-A (Espacenet English translation, downloaded Jul. 2020) (Year: 2020).*

* cited by examiner

*Primary Examiner* — Mark V Stevens

(57) ABSTRACT

The method includes treating bone and joint diseases with a composition which includes collagen, essential minerals, and mineral lactate which were derived from the bones of crocodilos reptilia (crocodile). Crocodile collagen is made of a different ratio of amino acids than mammalian collagen which may be at least partly responsible for its therapeutic properties. The composition further includes a mixture of herbs. The mixture of herbs may include Clinacanthus nutans, Eclipta prostrata, Drynaria rhizome, and Auricularia polytricha. The herbs in the mixture of herbs each has one or more of the following properties: anti-inflammatory, analgesic, bone formation enhancement, and increases the number of osteoblast proliferation without impacting the number or activity of osteoclasts. The composition may also include essential minerals which are important for bone formation. This composition may be useful to treat or prevent several common bone or joint diseases including osteoporosis, arthritis, and osteogenesis imperfecta.

19 Claims, 1 Drawing Sheet

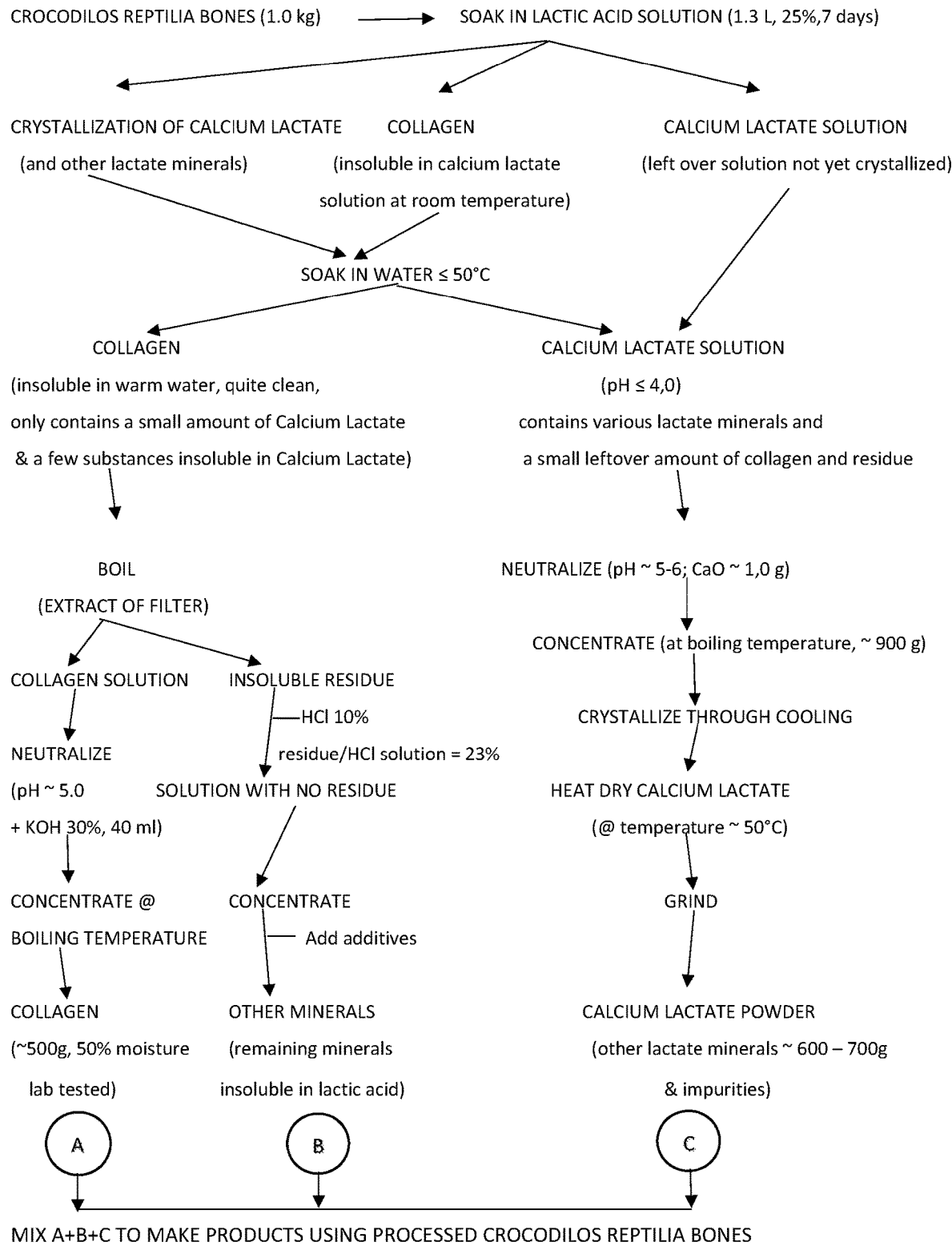

COMPOSITION AND METHODS FOR TREATING BONE AND JOINT DISEASE INCLUDING EXTRACT FROM CROCODILOS REPTILIA AND HERBS

BACKGROUND

Field of the Invention

This disclosure relates to compositions and methods of using the compositions to treat bone and joint disease.

Background of the Invention

Bone and joint disease cause significant pain as well as the loss of mobility, productivity, and quality of life. A variety of bone and joint diseases are known, including, but not limited to osteoporosis, arthritis (rheumatoid arthritis and osteoarthritis), and osteogenesis imperfecta. A large number of treatments exist for bone and joint disease which are associated with a variety of efficacies, different mechanisms of action, and unpleasant side effects.

Joints include cartilage, ligaments, tendons, joint capsules, and cavities with synovial fluid. Cartilage gives the joint freedom of movement by decreasing friction. It acts as a protective cushion which helps to reduce vibration and enable the bones of a joint to easily glide over one another with very little friction. Ligaments work like elastic bands connecting the bones together while tendons connect bones to muscles. Synovial fluid in the joint cavity absorbs friction and provides nutrients to the cartilages.

Articular cartilage, a resilient and smooth elastic tissue, is made up of two main components: cartilage compounds in a basic substrate. Cartilage compounds are not reproduceable/regeneratable after adulthood. No new cells form to replace dead cells. Because articular cartilage does not contain blood vessels or nerves, it is not nourished directly by the blood but only through the osmosis mechanism from the bones, synovial membrane and fluid. Therefore, cartilage can be easily degenerated over time without warning signs.

Cartilage, ligaments, and tendons are affected in inflamed and degenerative joints. A comprehensive method of treatment will ideally work on all of these parts of the joint.

Bone is made up of both organic substances that bind the bone elements together (including collagen fibers and bone cells) and minerals (including calcium, phosphorus, magnesium, and potassium). The type I collagen fibers within the organic substances bind the minerals together, which as a result, produces a healthy skeleton. In the absence of bone collagen, calcium cannot be absorbed into the bones, thus reducing the stiffness and flexibility of bones. Consequently, minerals settle in the joint region causing bone spurs. In the absence of collagen, the bone will gradually become porous, brittle, resulting in pain and often breakage.

Loss of bone collagen is the main cause of osteoporosis in adults and in osteoarthritis. Bone collagen gradually decreases after the age of 40, and the older the age, the more severe the bone density deficiency.

Traditional therapies for bone and joint disease primarily treat one or both of the bone's main components: organic substances (including collagen) and minerals. In addition, these therapies inhibit the growth of osteoclasts. However, these methods result in many cardiovascular and gastric side effects and do not conform to the physiopathology of osteoporosis. In addition, classical therapies facilitate the increase of mineral density in bones which makes bones harder, less elastic, thus more prone to breakage.

BRIEF SUMMARY OF THE INVENTION

The present disclosure describes a method of treating or preventing bone and joint disease by administering a composition that includes collagens, a mixture of herbs, mineral lactate, and essential and trace minerals. The collagen may include collagen types I, II, and III. The collagen may be extracted from the bones of crocodilos reptilia. In some embodiments, the mineral lactate includes calcium lactate.

In some embodiments, the composition includes the mixture of herbs in the following relative ratio: Clinacanthus nutans:Eclipta prostrata:Drynaria rhizome:Auricularia polytricha in a relative ratio of 1.5:1.5:2:2.

In some embodiments, the ratio of collagen+mineral lactate+essential and trace minerals: mixture of herbs is 6:7.

In some embodiments, the essential minerals may be derived from the bones of crocodilos reptilia. In some embodiments, the essential minerals may include calcium, phosphorus, magnesium, and potassium.

The disclosed method includes the step of administering to a subject in need thereof an effective amount of the disclosed composition. In some embodiments, the disclosed composition is administered orally.

In some embodiments, the subject may be a human. In some embodiments, the subject may be a non-human primate. In some embodiments, the subject may be a non-human vertebrate. In some embodiments, the subject may be a juvenile non-human vertebrate or a human child. In some embodiments, for example, when the subject is being treated for osteoporosis, the subject may be a postmenopausal female.

In some embodiments, the method may prevent or treat osteoporosis. In this embodiment, the subject may have or be at risk of developing osteoporosis. In this embodiment, the subject may be a postmenopausal female although the method may be used to treat premenopausal females or males.

In some embodiments, the method may prevent or treat arthritis. In this embodiment, the subject may have or be at risk of developing arthritis. The arthritis may be either osteoarthritis or rheumatoid arthritis.

In some embodiments, the method may treat osteogenesis imperfecta. In this embodiment, the subject may have osteogenesis imperfecta. In this embodiment, the subject may be a juvenile non-human vertebrate or a human child. However, adults with osteogenesis imperfecta may be the subject in this embodiment as well.

BRIEF DESCRIPTION OF THE DRAWINGS

In order that the advantages of the invention will be readily understood, a more particular description of the invention briefly described above will be rendered by reference to specific embodiments illustrated in the appended drawing. Understanding that this drawing depicts only a typical embodiment of the invention and is not therefore to be considered limiting of its scope, the invention will be described and explained with additional specificity and detail through use of the accompanying drawing.

FIG. 1 is a flow chart illustrating an embodiment of a method of extracting components from crocodile bones which may be included in the disclosed composition.

DETAILED DESCRIPTION OF THE DISCLOSURE

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "collagen" means a full or partial collagen protein, including collagen types I, II, and III.

While this invention is susceptible of embodiment in many different forms, there is shown in the drawing, which will herein be described in detail, a specific embodiment with the understanding that the present disclosure is to be considered as an exemplification of the principals of the invention and is not intended to limit the invention to the illustrated embodiment.

The disclosed composition and method of its use work simultaneously on the organic and mineral substances of the bones, in tandem with the increased activity of osteoblasts without suppressing the regular and natural activities of osteoclasts.

A strong and healthy bone and joint system requires sufficient collagen peptides (including collagen types I, II and III). They are the main components which bind bone minerals. When collagen peptides are combined with the herbs as disclosed herein, the disclosed composition results in new bone cells, increased bone density, increased cartilage formation, prevents degenerative joint diseases, and relieves pain. These activities result in restored limb movement and agility, maintained strength of the muscular-joint-ligament system, and reduced falls and bone fractures.

We disclose a composition and method of using the composition to treat and prevent bone and joint disease. The composition may include collagen, including, but not limited to, types I, II, and III. The collagen may be derived from the bones of crocodilos reptilia (crocodile).

Collagens extracted from the bones of crocodilos reptilia may be extracted using methods known in the art and used in the composition and methods disclosed herein. However, we disclose herein a method for extracting collagens and other components of the described composition. This method, in our hands, result in a greater yield than methods known in the art.

Collagens included in the disclosed composition and methods prevent degenerative joints, loss of articular cartilage, and reduce pain and inflammation. The collagens result in increased production of new bone cells, including osteoblasts, and increase bone density. Additionally, the collagens provide a platform for minerals needed for ossified bone to bind. They also increase the durability of ligaments, tendons, and increase muscle tone.

Moreover, the collagens work with the herbs discussed in more detail below to provide the preventative and therapeutic benefits of the composition and methods disclosed herein. Two of the herbs, clinacanthus nutans and eclipta prostrata improve liver functions and improve the body's ability to metabolize nutrients (sugar, protein and fat) more effectively. The collagens also act as an appetite suppressant. This combination of activities results in a leaner body which is helpful in developing and maintaining a healthy bone and joint system.

The disclosed composition may additionally include Drynaria rhizome. This herb stimulates formation of bone-forming cells, including osteoblasts, relieves pain, and reduces inflammation.

In some embodiments the mixture of herbs may include Auricularia polytricha. With its slippery, blood circulation enhancement attributes, Auricularia polytricha delivers the other active substances and oxygen through the body's arteries to alleviate pain and heal joints: This herb cleanses the walls of arteries and veins enhancing blood circulation, especially cerebral circulation, which allows ease of transport of other active substances within the disclosed composition to the affected areas. Additionally, Auricularia polytricha absorbs minerals, impurities in the intestinal tract, dissolves stones, and prevents the formation of plaques, platelets, blood clots.

Table 1 below describes the herbs which may be included in the mixture of herbs as well as examples of their biological activities and uses. The "uses" listed in Table 1 is not meant to be inclusive of all biological activities or practical uses of each herb. The biological activities of each herb in the mixture of herbs complement each other to result in the preventative and therapeutic activity of the disclosed composition and methods of its use.

TABLE 1

Herbs in an Embodiment of the Composition and Their Uses

| HERBAL INGREDIENT | USES |
| --- | --- |
| Clinacanthus nutans | Anti-inflammatory, analgesic, liver detoxification, shorten bone healing period after fracture |
| Eclipta prostrata | Increases bone formation, pain relief, liver detoxification, anti-inflammatory |
| Drynaria rhizome | Stimulates bone-forming cells, including osteoblasts, relieves pains and inflammation |
| Auricularia polytricha | Helps digest food, fight inflammation, detox the body, prevent the formation of plaques, platelets, blood clots, cleanse walls of arteries and veins, enhance blood circulation, especially cerebral circulation. |

The herbs included in the mixture of herbs may be provided in the composition in a variety of relative ratios. In some embodiments, the herbs in the mixture of herbs may be provided in the following relative ratio: Clinacanthus nutans:Eclipta prostrata:Drynaria rhizome:Auricularia polytricha in a relative ratio of 1.5:1.5:2:2

The composition may further include one or more mineral lactates. As used herein, "mineral lactate" means a soluble salt created by the reaction of lactic acid with a mineral. In some embodiments, the mineral lactate may be calcium lactate. In some embodiments, the mineral lactate may include magnesium lactate.

The composition may further include one or more essential and trace minerals. In some embodiments, the essential minerals may include one or more minerals on the following list of minerals: calcium, phosphorus, magnesium, and potassium. In some embodiments, the essential minerals may be in their soluble forms. "Trace minerals" is used herein as is commonly used in the art. Trace minerals may include one or more minerals on the following list: iron, manganese, chromium, cobalt, copper, fluoride, iodine, molybdenum, selenium, and zinc.

The components of the disclosed composition may be provided in a variety of relative ratios. In some embodiments, the relative ratio of collagen+mineral lactate+essential and trace minerals: mixture of herbs is 6:7.

Referring to FIG. 1, we disclose a method of extracting bones of crocodilos reptilia to derive ingredients used to produce the disclosed composition. In this example, 1.0 kg of bone from crocodilos reptilia was soaked in 1.3 L of 25% lactic acid solution for seven days. Three fractions resulted from this treatment. A first fraction included crystalized calcium lactate. This fraction included other mineral lactates, for example, magnesium lactate. A second fraction included collagen which is insoluble in calcium lactate solution at room temperature. The first and second fractions were then combined and soaked in water at a temperature equal to or less than 50° C. The third fraction was calcium lactate solution which included calcium lactate that had not crystalized.

The combination of first and second fractions resulted in insoluble collagen which, when separated, comprised very little calcium lactate. In some embodiments, separation may be performed by filtering.

The soluble fraction of the combination of the first and second fractions was calcium lactate solution which may include other mineral lactates, for example, magnesium lactate. A small amount of collagen may be carried over into this soluble fraction. This solution may be combined with the calcium lactate solution of the third fraction produced by soaking the bone in lactic acid solution.

Next, the separated, insoluble collagen was boiled producing a collagen solution and an insoluble residue. The collagen solution was neutralized to a pH of approximately 5.0 with potassium hydroxide (KOH, 30%, 40 ml) then concentrated at boiling temperature. This produced the final collagen product, marked "A" in FIG. 1.

The insoluble residue resulting from the boiling step was then neutralized with 10% hydrochloric acid (HCl). This step resulted in a solution with no solid residue. The solution was then concentrated using a vacuum evaporator. As one of skill in the art will readily understand, other methods of concentration may be used to increase the concentration of the solution according to this method. Additives were then added to the concentrated solution. In this embodiment, the additives included soluble starch which aids in the drying process used to produce granules. Other additives included $Ca_3(PO_4)_2$ for anti-bonding. Minerals which were insoluble in lactic acid were then removed from the solution. This produced the mineral component referred to as "B" in FIG. 1.

Referring back to the combined calcium lactate solution, this solution was neutralized to a pH of approximately 5.0-6.0 by adding approximately 1.0 g of calcium oxide (CaO). The solution was then concentrated at boiling temperature using a vacuum concentrator although other means of concentrating the solution may be used as known in the art.

The solution was then cooled which caused the calcium lactate in the solution to crystalize. The calcium lactate crystals were dried by heating to approximately 50° C. The dried calcium lactate crystals were then ground to produce a powder referred to as "C" in FIG. 1.

The fractions "A," "B," and "C" may be combined with the herbal mixture to produce the disclosed composition and used to treat or prevent bone and joint disease according to methods disclosed herein.

Table 2 below provides the relative amounts of each amino acid identified in a collagen sample produced by extracting the bones of crocodilos reptilia according to the method disclosed in FIG. 1 (fraction "A" of FIG. 1). The collagen fraction was isolated from the bones of crocodilos reptilia and analyzed to quantify each of the amino acid shown in Table 2. The numbers in Table 2 represent the grams of each amino acid that were found to be present in 100 g of the collagen fraction.

TABLE 2

| | Amino Acids in Collagen Fraction A | |
|---|---|---|
| | AMINO ACIDS* | g/100 g |
| 1 | Alanine | 3.64 |
| 2 | Arginine | 2.45 |
| 3 | Aspartic acid | 1.64 |
| 4 | Glutamic acid | 3.12 |
| 5 | Glycine | 6.59 |
| 6 | Histidine | 0.21 |
| 7 | Isoleucine | 0.42 |
| 8 | Leucine | 0.66 |
| 9 | Lysine | 1.18 |
| 10 | Methionine | 0.26 |
| 11 | Phenylalanine | 0.57 |
| 12 | Proline | 3.92 |
| 13 | Serine | 1.1 |
| 14 | Threonine | 0.59 |
| 15 | Tyrosine | 0.1 |
| 16 | Valine | 0.57 |
| | Total Amino Acids | 27.02 |
| | Protein | 29 |

Moisture Content: 56.5%

Table 3 below provides the mineral content of each fractions "A," "B," and "C" produced according to the extraction method disclosed in FIG. 1. The fractions shown in Table 3 are the collagen fraction (fraction "A" in FIG. 1), the essential and trace mineral fraction (fraction "B" in FIG. 1), and the mineral lactate fraction (fraction "C" in FIG. 1). Each fraction was isolated from the bones of crocodilos reptilia and submitted to an analytical laboratory. The numbers in Table 3 represent the grams of each mineral that were found to be present in 100 g of each fraction.

TABLE 3

Grams of Minerals in Fractions Extracted from Crocodilos Reptilia Bone

| | COLLAGEN FRACTON A | ESSENTIAL & TRACE MINERALS FRACTON B | MINERAL LACTATE FRACTON C |
|---|---|---|---|
| Moisture Content UOM g mineral/ 100 g of fraction | 56.5% | 2.7% | 23.2% |
| Calcium | 0.28 | 30.4 | 15.2 |
| Potassium | 1.47 | 1.52 | 0 |
| Magnesium | 0.034 | 0.11 | 0.39 |
| Phosphorus | 0 | 14.8 | 3.64 |
| Total Essential Minerals | 1.784 | 46.83 | 19.23 |
| Amino Acids | 27.02 | | |
| Protein | 29 | 13.1 | 2.05 |

The composition disclosed herein may be used to prevent or treat bone and joint diseases according to methods disclosed herein. In some embodiments, the method includes administering the disclosed composition orally to a subject in need. In some embodiments, the composition may be administered to the subject in need once per day, twice per day, or three times per day. In some embodiments, the composition may be administered to the subject in need once per week or once per month.

In some embodiments of the disclosed method, the subject may be a human. The human may be an adult or child. In some embodiments, the subject may be a non-human vertebrate, adult or juvenile. In some embodiments, the subject may be a non-human primate, adult or juvenile.

A method of using the disclosed composition to treat or prevent osteoporosis is disclosed herein. The pathology of osteoporosis includes reduced bone formation, at least in part because osteoblasts are working less efficiently, while the process of bone resorption continues almost normally. There is a reduction in collagen type I which reduces mineral binding to bone and, thus, reduces bone strength. There may be insufficient nutrient absorption by the digestive system resulting in a deficiency of amino acids, for example, proline, alanine, glycine, and lysine, which are required for the body to form proteins including collagen. There may be increased oxidants and chronic, low-level inflammation. There may be reduced blood circulation which is required to nourish bones, joints and ligaments. Osteoporosis may occur after the onset of menopause in women or in response to a disorder of the endocrine system, for example, low estrogen or testosterone, hyperthyroidism, or hyperparathyroidism.

A common pharmaceutical treatment for osteoporosis is bisphosphonate therapy. However, bisphosphonates have many side effects, including those involving the gastrointestinal tract and jawbone necrosis. Additionally, bisphosphonate therapy is inconvenient because the patients must sit or stand over 30 minutes after taking the pills to prevent acid reflux.

Another common treatment for osteoporosis is a combination of calcium and vitamin D supplements. An advantage of this treatment is that it increases bone mass. However, while the bones become hard, they are less flexible as evidenced by an increase in bone fracture rate.

The disclosed method includes the step of providing the disclosed composition to a subject who has or is at risk of developing osteoporosis. In some embodiments, the subject may be a postmenopausal female. In some embodiments, the subject may have been diagnosed with a disorder of the endocrine system. The subject may be a human, a non-human primate, or a non-human vertebrate.

The method may include instructing the subject to consume the disclosed composition orally. In some embodiments, the method may include the step of administering the disclosed composition to the subject. In some embodiments, the disclosed composition may be administered to the subject once per day, twice per day, or three times per day. In some embodiments, the disclosed composition may be administered to the subject once per week or once per month.

Advantages of this method of preventing or treating osteoporosis over current methods include that it creates a positive impact on bone creation, including supplying collagen to bone tissues, which facilitates the adhesion of inorganic minerals to bones. Additionally, it promotes the activity of bone generating cells (osteoblasts). Furthermore, unlike bisphosphonates, it does not inhibit the activities of osteoclasts. This is relevant because it is critical that osteoclasts continue breaking down bone tissues, thus facilitating osteoblasts to replace old bone cells with new osteocytes.

In summary, the disclosed method of treatment of osteoporosis is built in accordance with the pathophysiology of osteoporosis, it is rarely associated with untoward effects, and it avoids the use of inorganic minerals derived from external sources.

A method of using the disclosed composition to treat or prevent arthritis is disclosed herein. There are multiple types of arthritis, including osteoarthritis and rheumatoid arthritis. The pathology of arthritis includes stiff, less flexible joints and loss of synovial fluid which creates friction and scars in joint cartilage. Minerals may settle around the joints, resulting in the formation of bone spurs. Arthritis may be associated with a loss of cartilage in joints and porous bones. Additionally, there may be small structure changes in ankle joints. Arthritis may be associated with osteoporosis due to lack of collagen type which reduces the area onto which minerals bind.

The disclosed composition includes collagen and minerals which increase bone formation and anti-inflammatory herbs. These ingredients impact the disease mechanism of arthritis.

The method may include the step of instructing a subject having arthritis, either osteoarthritis or rheumatoid arthritis, to consume the disclosed composition orally. In some embodiments, the method may include the step of administering the disclosed composition to the subject. In some embodiments, the disclosed composition may be administered to the subject once per day, twice per day, or three times per day. In some embodiments, the disclosed composition may be administered to the subject once per week or once per month.

A method of using the disclosed composition to treat or prevent osteogenesis imperfecta is disclosed herein. Osteogenesis imperfecta is also known as brittle bone disease because it results in bones that break easily. Those suffering from this disease may also have loose joints.

Current treatments of osteogenesis imperfecta include bisphosphonates, surgery, and physiotherapy. Bisphosphonates, however, are associated with untoward effects as described elsewhere herein.

The disclosed method includes the step of providing the disclosed composition to a subject who has osteogenesis imperfecta. In some embodiments, the method may include the step of administering the disclosed composition to the subject. In some embodiments, the subject may be a juvenile. In some embodiments, the subject may be a human child. In some embodiments, the subject may be a human, a non-human primate, or a non-human vertebrate.

The method may include the step of administering the disclosed composition to the subject orally. In some embodiments, the disclosed composition may be administered to the subject once per day, twice per day, or three times per day. In some embodiments, the disclosed composition may be administered to the subject once per week or once per month.

Examples

Treatment of Osteoporosis in Postmenopausal Women

Study subjects were eighteen (18) postmenopausal women divided into 2 groups:
  Group 1: 12 subjects, age: 67.3±10, taking 700 mg of extract of crocodile bones/day at 16% moisture content;
  Group 2: 6 subjects, age: 74±9.2, taking calcium and vitamin D.

Results after 3 months of treatment by measuring bone mineral density (DXA):
  Group 1:
    Before taking extract: DXA=−3.56±0.83;
    After taking extract: DXA=−2.47±2.35 (P-value: 0.003).
  Group 2:
    Before taking calcium and vitamin D: DXA=−3.6±0.67;
    After: DXA=−2.88±1.2 (P-value: 0.05).

Treatment of Osteoarthritis (OA)

Study subjects were forty one (41) people diagnosed with OA based on clinical examinations and X-Rays. Subjects were given 700 mg of extract of crocodile bones/day at 16% moisture content. The extract of crocodile bones included approximately 70% collagen.

Results after 2 weeks of taking extracts of crocodile bones were as follows:
  Pain relief: 78.06% (P-value <0.01);
  Mobility Recovery: 70% (P-value <0.01);
  No changes in liver and kidney function tests;
  No detection of side effects: epigastric pain, gastrointestinal disorders, heartbeat and blood pressure measurements did not change before and after taking the pills.

Treatment of Osteogenesis Imperfecta (OI) in Children

Study subjects included over two hundred (200) diagnosed with OI. Subjects were given 450 mg/day of extract for time periods ranging from 2 weeks to 1 month.
  Results:
  Pain Relief: 95%;
  Subjects stop taking non-steroid anti-inflammatory drug after 2 weeks;
  The frequency of fractures decreased by 78% during the course of treatment;
  Mobility Recovery (e.g., walking unassisted): 66%;
  Better physical development.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of treating bone and joint disease comprising administering to a subject in need thereof an effective amount of a composition comprising the following:
   a. collagen derived from bones of crocodilos reptilia;
   b. a mixture of herbs, the mixture of herbs comprising:
      i. Clinacanthus *nutans;*
      ii. Eclipta *prostrata;*
      iii. Drynaria rhizome; and
      iv. *Auricularia* polytricha;
   c. mineral lactate; and
   d. essential and trace minerals
   wherein the mixture of herbs comprises Clinacanthus *nutans*: Eclipta *prostrata*: Drynaria rhizome: *Auricularia* polytricha in a relative ratio of 1.5:1.5:2:2.

2. A method of treating bone and joint disease, comprising administering to a subject in need thereof an effective amount of a composition comprising the following:
   a. collagen derived from bones of crocodilos reptilia;
   b. a mixture of herbs, the mixture of herbs comprising:
      i. Clinacanthus *nutans;*
      ii. Eclipta *prostrata;*
      iii. Drynaria rhizome; and
      iv. *Auricularia* polytricha;
   c. mineral lactate; and
   d. essential and trace minerals;
   wherein the composition further comprises trace minerals, wherein a ratio of a+c+d:b is 6:7.

3. The method of claim 1, wherein the collagen comprises collagen type I, type II, and type III.

4. The method of claim 1, wherein the essential and trace minerals comprise calcium, phosphorus, magnesium, and potassium.

5. The method of claim 1, wherein the essential and trace minerals are derived from the bones of crocodilos reptilia.

6. The method of claim 1, wherein the composition is administered orally.

7. The method of claim 1, wherein the composition is administered once per day.

8. The method of claim 1, wherein the bone and joint disease consists of osteoporosis.

9. The method of claim 8, wherein the subject is a postmenopausal female.

10. The method of claim 8, wherein the subject is a nonhuman vertebrate.

11. The method of claim 1, wherein the bone and joint disease consists of osteogenesis imperfecta.

12. The method of claim 11, wherein the subject is a juvenile non-human vertebrate.

13. The method of claim 11, wherein the subject is a human child.

14. The method of claim 1, wherein the bone and joint disease consists of arthritis.

15. The method of claim 14, wherein the arthritis consists of osteoarthritis.

16. The method of claim 14, wherein the arthritis consists of rheumatoid arthritis.

17. The method of claim 1, wherein the subject is a human.

18. The method of claim 17, wherein the subject is a human child.

19. The method of claim 1, wherein the subject is a nonhuman vertebrate.

* * * * *